United States Patent [19]

Sato et al.

[11] Patent Number: 4,686,974

[45] Date of Patent: Aug. 18, 1987

[54] BREATH SYNCHRONIZED GAS-INSUFFLATION DEVICE AND METHOD THEREFOR

[75] Inventors: Toru Sato; Naoto Okazaki; Toshihisa Hasegawa, all of Yonago; Katsumasa Fujii; Kazukiyo Takano, both Okayama, all of Japan

[73] Assignee: Tottori University, Tottori, Japan

[21] Appl. No.: 904,021

[22] Filed: Sep. 2, 1986

[30] Foreign Application Priority Data

Oct. 18, 1985 [JP] Japan .................................. 60-231059

[51] Int. Cl.$^4$ ............................................. A61M 16/00
[52] U.S. Cl. ............................ 128/204.23; 128/207.18
[58] Field of Search ...................... 128/204.21, 204.23, 128/204.24, 204.25, 204.26, 205.24, 207.18

[56] References Cited

U.S. PATENT DOCUMENTS

| 2,830,579 | 4/1958 | Saklad et al. | 128/204.23 |
| 4,567,888 | 2/1986 | Robert et al. | 128/204.26 |
| 4,570,631 | 2/1986 | Durkan | 128/204.23 |
| 4,584,996 | 4/1986 | Blum | 128/207.18 |
| 4,592,349 | 6/1986 | Bird | 128/204.25 |

Primary Examiner—Henry J. Recla
Attorney, Agent, or Firm—Spencer & Frank

[57] ABSTRACT

Steady insufflation of a gas starts before the beginning of each inhalation, and a pulse-like peak flow insufflation of the gas is superposed on the steady insufflation for a short period of times at the beginning of the inhalation, and the steady insufflation is terminated before the end of the inhalation, so as to improve the inhalation efficiency of insufflated gas extremely.

5 Claims, 9 Drawing Figures

Respiratory Signal

Respiratory Period

Steady Flow Waveform

Peak Flow Waveform

Total Flow Rate Curve

FIG.3A _PRIOR ART_
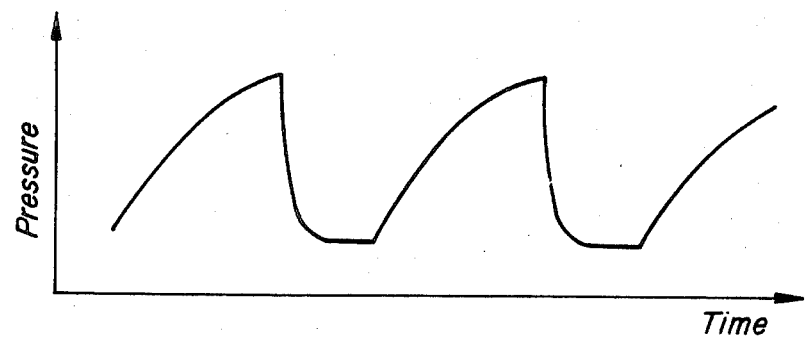
FIG.3B _PRIOR ART_
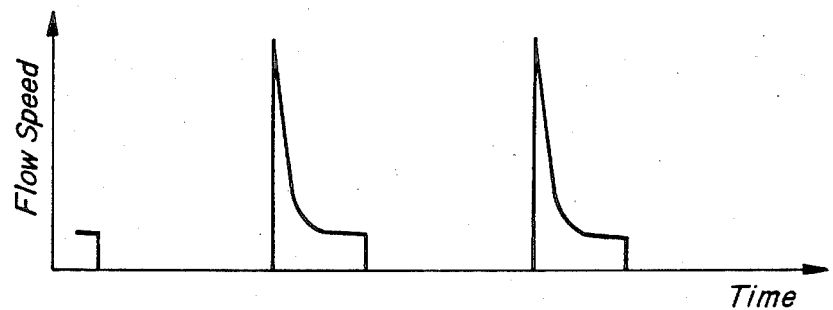
FIG.3C _PRIOR ART_
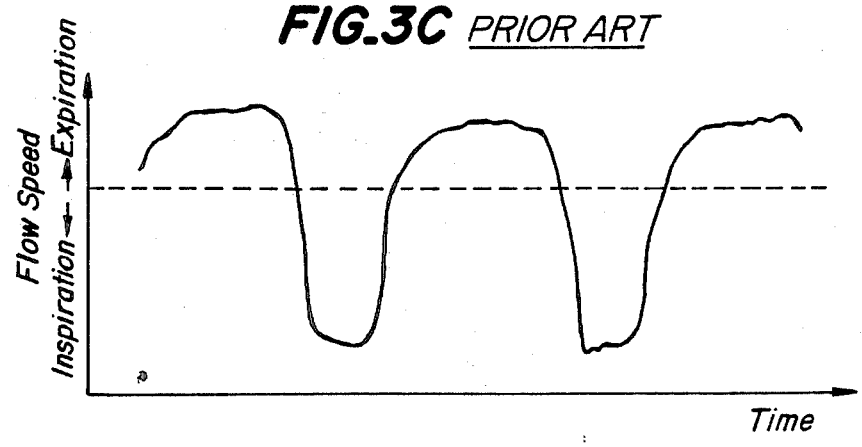

BREATH SYNCHRONIZED GAS-INSUFFLATION DEVICE AND METHOD THEREFOR

BACKGROUND OF THE INVENTION

1. Field of the Invention

This invention relates to a device and a method for insufflating oxygen gas or anesthetic gas such as laughing gas to the respiratory system of a living body in synchronism with his breathing. More particularly, the invention relates to maximization of the effect of gas insufflation by improving of the gas inhalation efficiency so as to be matched in the optimum condition.

2. Related Art Statement

In general, there are two methods for a living body, e.g., a patient, to inhale a gas such as oxygen gas or anesthetic gas; namely, the closed type and the open type. The closed type uses the so-called facemask or an endotracheal tube and supplies the gas to the living body through a breathing circuit system, which includes the respiratory organs of the living body and the gas supply device, while airtightly separating the system from the atmosphere. This closed type method has an advantage in its high inhaling efficiency. However, the closed type method has a shortcoming of causing irritation or discomfort on the side of the patient or the like because of the covering of his mouth and nose air-tightly and the direct insertion of foreign bodies into his trachea. Accordingly, the closed type method has been used mainly for unconscious and seriously sick patients who need artificial and augmented ventilation.

On the other hand, the open type method inserts the tip of a gas supplying tube into the nostril or the mouth of a patient so as to supply the gas while keeping the above-mentioned respiratory circuit system open to the atmosphere. Thus, parts to be in tight contact with the face or upper airway of the patient for making an airtight system are eliminated, and the irritation or discomfort on the side of the patient is reduced and the patient is allowed to speak, eat or drink freely during the inhalation treatment. Accordingly, this open type method is mainly used for mild cases in which self-breathing is possible and dependable.

In the conventional closed type gas-breathing apparatus and method, gas is supplied in response to the breathing of the living body by detecting the gas pressure changes in the closed breathing circuit system. However, in the conventional open type gas-breathing apparatus and method, it is difficult to detect the pressure change in the breathing circuit system, and in most cases, the gas is supplied at a steady flow rate regardless of the breathing of the living body. Thus, the gas is constantly insufflated into the living body even during the exhalation, and discomfort has been cause to him. Besides, a large part of the gas supplied during the exhalation period of the living body is wasted by being discharged to the atmosphere without being used. In addition, the open type gas-insufflation apparatus is susceptible to undue reduction of the concentration of the gas being inhaled because the tip of the gas-supply tube is open and directly communicates with the atmosphere. To cope with such reduction of the gas concentration to be inhaled, it has been practiced to increase the flow rate of the such constantly fed gas.

To overcome such shortcomings, the inventors proposed in their Japanese Patent Laying-open Publication No. 8,972/84 a breath-synchronized open type gas-insufflation system, in which the gas was supplied only during inhalation periods in synchronism with the breath of the living body, and the inventors disclosed that the amount of insufflating gas needed to maintain the equivalent efficiency of oxygenation was greatly reduced. More particularly, the inventors proposed an efficient gas-insufflation by periodically interrupting the gas supply in synchronism with the breaths of the living body so as to insufflate the gas only during his inhalation periods.

In an ideal gas insufflation, the amount of gas to be insufflated should be changed in coincidence with variation of the inhaled air volume in each inhalation, which not only depends on the inherent respiration pattern of the individual living body but also depends on his emotional, intentional and physical conditions. If the amount of the inhaled gas can be controlled in the above-mentioned manner, the gas concentration in the air inhaled into the living body can be always kept at a high level. In readily, however, it is almost impossible to realize the above ideal gas insufflation by accurately measuring the volume of inhaled gas for each living body at each moment and keeping the flow rate of the insufflated gas in good agreement with the measured volume of the inhaled gas, because the respiration pattern varies depending on individual living bodies, and the respiration pattern of a living body is ever changing depending on various physical, intentional and emotional activities on each time of measurement. Thus, there has been a limit in improvement of the gas-insufflation efficiency.

The inventors further suggested in their Japanese Patent Laying-open Publication No. 253,495/1984 a breath-synchyronized concentrated-oxygen supplier which simultaneously improved both the gas (oxygen in the Publication) production (concentrating) efficiency of the oxygen concentrator on the side of a machine and gas-inhalation efficiency on the side of a living body to whom the device feeds the gas. The improvements are based on predetermined of a gas-feeding pattern which matches the average of several respirations immediately before each insufflation, elimination of gas waste by stopping the gas supply at an end portion of each inhalation, and maintenance of a comparatively high gas concentration in the feed gas by alternate use of a pair of oxygen concentrator columns of pressure swing adsorption type. It was noted that the gas inhaled by the living body at the end portion of each inhalation did not reach the effective part of his respiratory organ.

In the previously proposed breath-synchronized gas-insufflation devices, a high gas (e.g., oxygen) concentration is provided at the very beginning of each inhalation and wasteful gas supply at the end portion of each inhalation is eliminated. To maintain the high oxygen pressure, a pair of oxygen concentrator columns of pressure swing adsorption type are alternately used; namely, extracting oxygen from one column while regenerating the other column by purging with the product gas in an alternate manner. However, the previously proposed devices have a problem in that a maximum gas inhaling efficiency on the side of a living body is not always ensured, because the devices failed in providing continuous supply of a sufficient amount of gas at the beginning of each inhalation for matching the high gas inhaling capability available at that moment on the side of the living body.

SUMMARY OF THE INVENTION

Therefore, an object of the present invention is to obviate the above-mentioned shortcomings and problem of the prior art by providing a novel device and method for breath-synchronized gas insufflation based on the inventors' fiding that the gas inhaled by a living body at the beginning of his inhalation reaches a deep portion of his respiratory organ so as to contribute to the improvement of gas-inhalation efficiency on the side of the living body.

The device and method of the invention are featured in that the gas is supplied to the living body at the end portion of his exhalation so as to replace the residuals of the exhaled air in the nasal cavity, mouth and trachea with the gas thus supplied while sufficiently raising the concentration of the gas to be inhaled, that a short pulse-like increase of gas insufflation is provided at the beginning of the inhalation so as to deliver high-concentration gas to deep portion of his respiratory organ for maximizing the gas-inhalation efficiency on the side of the living body, and that the gas insufflation is ended before the termination of the inhalation so as to eliminate gas waste. It is noted that the gas inhaled by a living body at the end portion of the inhalation remains at a dead space of his respiratory organ and is extracted to the outside atmosphere at the next exhalation without being used in his respiratory organ. The invention intends to fill the dead space of the respiratory organ with the atmospheric air but not with the gas being insufflated. Thus, both the gas-production efficiency on the side of the oxygen concentrating device and the gas-inhalation efficiency on the side of the living body are simultaneously improved.

The invention also provides for easy input of settings, such as a preset percentage of the exhalation period for allowing gas supply and a preset duration of the above-mentioned short pulse-like increase of gas insufflation, to the gas-insufflation device. Such input of the settings facilitates the maximization of the above efficiencies under various operating conditions.

To fulfil the above object, a preferred embodiment of the invention uses an operational controller having a microprocessor or central processing unit (to be referred to as CPU hereinafter) which receives electric signals from a sensor exposed to respiration of a living body. The sensor detects, for instance by temperature difference, the inhalation and exhalation of the living body, and provides output signals or respiration signals which represent such inhalation and exhalation in the respiration. The operational controller converts the respiration signals from analog to digital, and differentiates them with respect to time for determining their gradients. The period having a positive gradient of the respiratory signal is recognized as an exhalation period, while the period having a negative gradient of the respiratory signal is recognized as an inhalation period. The operational controller determines the lengths of average inhalation and exhalation periods over several respiration immediately preceding a specific respiratory cycle, and it renews such average periods for each new respiratory cycle of the living body and stores the renewed average periods as the respiratory pattern of the living body or as the time variation of the respiration.

Considering the average inhalation and exhalation periods, the operational controller carries out the gas insufflation; namely, it starts the gas insufflation before beginning of the inhalation phase so as to replace the residuals of the exhales air in certain living body cavities with the insufflated gas, then it provides a short pulse-like increase of the gas insufflation substantially at the beginning of each inhalation in synchronism with a sudden change of the respiration air speed so as to maximize the gas-inhalation efficiency on the side of the living body, and it ends the gas insufflation before termination of the inhalation phase so as to eliminate the gas waste by not feeding the gas to be trapped in a dead space of the living body at the end portion of his inhalation.

The operational controller copes with various changes in the operative conditions on real time basis. For instance, pseudo-respiration signals, such as those generated during conversation, are compared with the average signals, and when found unsuitable for the control, such pseudo-respiration signals may be elminated by a filler circuit (not shown). On the other hand, in the case of a special respiration such as a deep breath, the period of respiration is greatly increased, and the operational controller automatically extends the gas-insufflation period.

Preferably formation of the breath-synchronized gas-insufflation device of the invention are as follows.

(1) A sensor is disposed by the nostril of a living body for detecting his respiration and producing the respiration signals. An operational controller, having an amplifying portion and an operational portion, receives the respiration signals from the sensor and amplifies them in its amplifying portion and processes them in its operational portion so as to produce and deliver control signals to gas flow controllers disposed on the passage of the gas to be insufflated.

The operational controller controls first one of the gas flow controllers so as to intermittently supply gas flows of steady flow rate from the gas source in synchronism with the breathing periods of the living body. Second one of the gas flow controllers is connected in parallel to the first gas flow controller, and the operational controller controls the second gas flow controller so as to provide a short pulse-like gas insufflation at suitable timing. The controlled gas flows from the two gas flow controllers are combined and insufflated to the living body. The operational controller controls the two gas flow controllers in a suitable manner so as to effect high-efficiency of gas inhalation in synchronism with the breath of the living body.

(2) The operational controller continuously redetermines and stores an average exhalation period and an average inhalation period over several respirations immediately preceding each respiratory cycle, and it controls the intermittent gas insufflation based on the thus stored distinctive average exhalation and inhalation periods, so as to start the gas insufflation at a last portion of the exhalation phase before beginning of the inhalation phase and to end it before termination of the inhalation phase before beginning of the exhalation phase.

(3) The operational controller differentiates the respiration signals with respect to time and determines the beginning of the inhalation by monitoring both the magnitudes and the polarity of the gradients of the respiratory signals, and the controller controls the gas flow controllers so as to provide a short pulse-like increase of the gas insufflation at the beginning of the inhalation when the gas-inhalation efficiency on the side of the living body is high.

(4) The two gas flow controllers for controlling the gas flow of steady flow rate and the short pulse-like increase of the gas insufflation may be replaced with a single gas flow control means having a suitable combination of throttle valve nd electromagnetically controlled solenoid valve for regulating both the flow rate and the duration of the gas insufflation. The device and method of the invention provide for insufflation of a desired gas, such as oxygen or laughing gas, in synchronism with the breathing of a living body, so as to realize the special effect of maximizing the gas-inhalation efficiency.

The breath-synchronized gas-insufflation device according to the present invention is particularly suitable for medical use, for instance, as a means for breath-synchronized inhalation treatment with oxygen or a means for laughing gas inhalation for hypalgesic inhalation anesthesia. With the device and method of the invention, a desired gas such as oxygen and laughing gas can be insufflated with a suitable timing at about the beginning of inhalatiion so as to ensure a maximum gas-inhalation efficiency on the side of a living body.

BRIEF DESCRIPTION OF THE DRAWINGS

For a better understanding of the invention, reference is made to the accompanying drawings, in which:

FIG. 3A through FIG. 3C are graphs showing variations of different quantities in a breath-synchronized gas-insufflation device of prior art.

Figure 1:
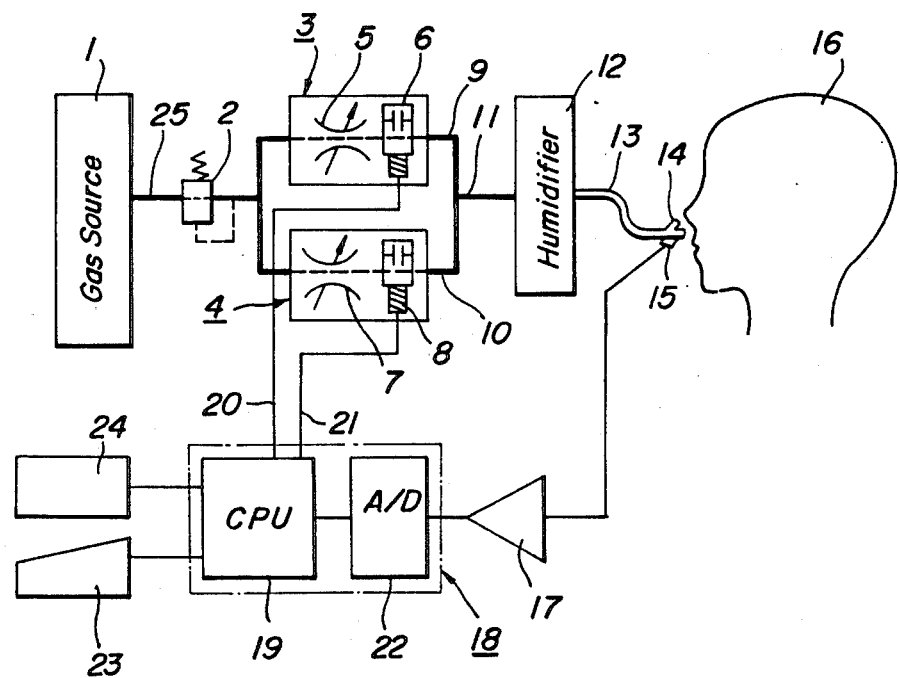
FIG. 1 is a schematic block diagram of a breath-synchronized gas-insufflation device according to the present invention.

Throughout different views of the drawing, 1 is a gas source, 2 is a reducing valve, 3 is a first gas flow controller, 4 is a second gas flow controller, 5, 7 are throttle valves, 6, 8 are solenoid valves, 9, 10, 13, 25 are gas pipes (or tubes), 11 is a junction, 12 is a humidifier, 14 is a nasal cannula, 15 is a respiration sensor, 16 is a patient, 17 is an amplifier, 18 is an operational controller, 19 is a central processing unit (CPU), 20, 21 are control output lines, 22 is an A/D converter, 23 is an input means, and 24 is a display unit.

DESCRIPTION OF THE PREFERRED EMBODIMENT

The invention will now be described in detail by referring to an embodiment illustrated in the accompanying drawing.

The breath-synchronized gas-insufflation device of the invention controls both the flow rate and the duration of gas flow at each respiration in a suitable manner. The hardware formation of the device of the invention is similar to that of the above-mentioned oxygen supplier of Japanese Patent Laying-open Publication No. 253,495/1984, except that a sophisticated valve means, such as a combination of a throttle valve and a solenoid valve, is used in the device of the invention.

In the oxygen supplier of the prior art, two oxygen concentrator columns are alternately used. More particularly, when oxygen-enriched gas is used for insufflation from one of the two columns acting as an oxygen source, the other column acts to increase the oxygen concentration therein by removing nitrogen from the air by adsorption. When the two columns are switched over, a part of the oxygen-enriched product gas, i.e. washing out nitrogen is delivered to the above other column for purging. Such alternate operation is repeated in a cyclic manner. When oxygen-enriched gas with an increased pressure after a non-feeding period as shown in FIG. 3A is released in synchronism with the quick change of air speed at the beginning of inhalation phase of the respiration of a living body as shown in FIG. 3C, the flow rate of oxygen for insufflation increases momentarily in the beginning of the release as shown in FIG. 3B. The increase of the oxygen flow rate, however, does not last long and drops quickly as shown in FIG. 3B.

It is known that the gas inhaled in the early part of the inspiratory phase is very effective in the living body, but with the oxygen flow rate change of FIG. 3B, sufficient amount of the gas may not be inhaled by the living body for certain types of the ever-changing respiratory pattern. Besides, when the gas insufflation starts at the beginning of the inhalation phase, there are residuals of exhaled air in the nasal cavity, mouth and dead space of the respiratory organ, and such residuals may be inhaled again so that the concentration of the desired gas at the beginning of the inspiratory phase is not necessarily high enough.

The above problem of the prior art may be overcome by combining a valve means including a throttle valve and an electromagnetically activated solenoid valve and an operational controller with a breath-synchronized gas-insufflation device similar to the above oxygen supplier of the prior art, and by regulating the valve means by the operational controller so as to produce the above-mentioned gas flow pattern of the invention. In practice, it is preferable to provide one valve means for regulating the gas flow at a steady flow rate with a preset duration and a separate valve means for regulating the short pulse-like increase of the gas insufflation with a preset duration so as to avoid rapid actuation of the throttle valve at each respiration. With the separate valve means for the steady flow rate and for the short pulse-like superimpose (superposition), the formation is simplified and the operation becomes steady, and the desired flow pattern can be obtained effectively.

Fundamental configuration of the breath-synchronized gas-insufflation device of the invention. based on the above principle is shown in FIG. 1, and its operation is shown in FIG. 2A through FIG. 2E.

The embodiment of FIG. 1 is for application of the present invention to medical use as an oxygen inhaler. Gas source 1 of this embodiment is an oxygen cylinder or an oxygen concentrator.

In the figure, the gas from the gas source 1 is delivered to a reducing valve 2 through a gas pipe 25. After being reduced to a suitable pressure, the gas is applied to parallel gas flow controllers, i.e., a first gas flow controller 3 and a second gas flow controller 4, so that the gas is insufflated to a patient 16 with a flow pattern produced by the controller 3 and 4. The first gas flow controller 3 has a semi-fixed throttle valve 5 and a solenoid valve 6. The throttle valve 5 is manually set so as to produce a gas flow waveform with a steady flow rate as shown in FIG. 2C. The coil of the solenoid valve 6 is controlled by a control signal on the control output line 20 from an operational controller 18 in such a manner that the gas flow there is controlled with the timing and duration as shown in FIG. 2C.

The second gas flow controller 4 also has a semi-fixed throttle valve 7 and a solenoid valve 8. The throttle valve 7 is manually set so as to produce a pulse-like gas flow waveform as shown in FIG. 2D. The coil of the solenoid valve 8 is controlled by a control signal on the control output line 21 from the operation controller 18 in such a manner that the gas flow there is controlled with the timing and duration as shown in FIG. 2D. The gas flow controllers 3 and 4 deliver gas to the gas pipes 9 and 10 respectively, and two gas flows are combined at a joint 11 of the gas pipes, so that a gas flow waveform of FIG. 2E is produced. A suitable amount of moisture is added to the gas flow from the joint 11 by a humidifier 12, and the thus moistened gas is insufflated to the nasal cavity of the patient 16 through the gas tube 13 and a nasal cannula 14.

As respiration sensor 15, such as a thermocouple, is mounted on the cannula 14, which sensor detects the temperature change in the air flow to and from the nostril of the patient 16 and produces electric signals representing such temperature changes. The electric signals from the sensor 15 are applied to the operational controller 18. Preferable examples of the respiration sensor 15 responsive to respiratory gas for producing electric signals representing the respiratory action are temperature-sensitive element like thermocouples which convert the temperature change between the exhalation and inhalation into electric signals, or pressure-sensitive element which convert the pressure difference between the exhalation and inhalation into a change in strain resistance. The strain resistance change can be measured by connecting it in a resistance bridge circuit so as to convert such strain resistance change into an electric current change.

In the illustrated embodiment, a thermocouple is used as the respiration sensor 15. Voltage change in the respiratory signal, i.e., the output signal from the thermocouple of the sensor 15, representing the temperature change in the respiratory air, is suitably amplified by an amplifier 17 and applied to the operational controller 18. The operational controller 18 has a CPU 19 and an A-D converter 22 for converting the analog value of the voltage change in the respiratory signal into a corresponding digital value. The CPU 19 includes a memory for storing a control program for the entire device, another memory for storing measured data and the result of arithmetic operations, and input port for receiving the digital value of the respiratory signal voltage as an input thereto, another input port for receiving input signals from an input means 23 such a keyboard which facilitates input of parameters of control operations which will be described hereinafter, an output port for delivering those signals to a display unit 24 which represent outputs of arithmetic operation for control and input values from the input means, and a driving circuit for the display unit.

Figure 2A:
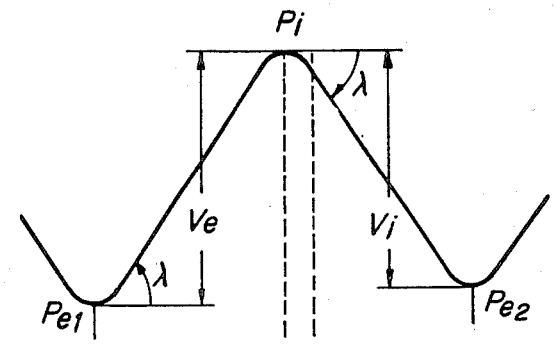
FIG. 2A through FIG. 2E are graphs showing signal waveforms and variation of quantities in the breath-synchronized gas-insufflation device of FIG. 1.
Figure 2B:
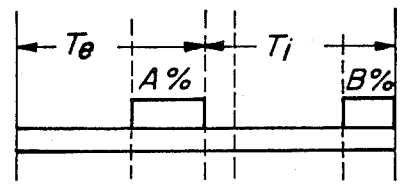
Figure 2C:
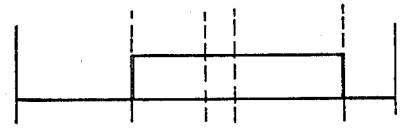
Figure 2D:
Figure 2E:
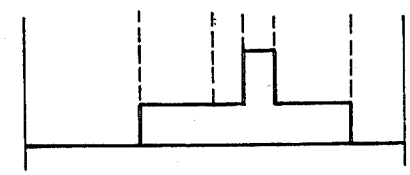

FIG. 2A shows an example of a respiratory signal in the device of FIG. 1, and FIG. 2B through FIG. 2E show examples of waveforms of set signals and gas flow control signals generated by the operational controller 18 in succession. The analog respiratory signal produced by the respiration sensor 15 has a waveform of FIG. 2A. During expiratory period, the temperature of the exhaled air increases due to the body temperature of the patient 16, and the respiration signal has an increasing voltage. During inspiratory period, the outside low-temperature air in inhaled and the voltage of the respiratory signal decreases. The respiratory signal with the voltage waveform of FIG. 2A is amplified by the amplifier 17 to a suitable level for application to the A-D converter 22 which converts it into digital data signal. The CPU 19 processes the digital data signal by the program stored therein while using the set values provided by the input means 23, so as to produce electric control signals on the control output lines 20 and 21 as a result of operational calculation. The control signals are to produce the above-mentioned gas flow patterns of the desired gas.

The display unit 24 displays both numerical values of input signals from the input means 23 such as ten-keys of a keyboard and alarm signals from various abnormality detectors mounted on the device of the invention. Some examples of the abnormality to be found by such detectors are abnormally long or abnormally short periods of respiration, and lack of the respiration signals over a period in excess of a certain preset length. The CPU has software mounted thereon for detecting such abnormally, and the detection of any of such abnormality is shown on the display unit 23.

The software of the CPU 19 for processing the respiratory signals thus obtained will be explained now. In the CPU 19, the respiratory signals obtained are differentiated with respect to time for determining the gradient $\lambda$ of the signal waveform. The period in which the gradient $\lambda$ is positive is recognized as the expiratory period, while the period with a negative gradient $\lambda$ is recognized as the inspiratory period. The point where the polarity of the gradient $\lambda$ turns from positive to negative is recognized as the inspiration-start point $P_i$, while the point where the polarity of the gradient $\lambda$ turns from negative to positive is recognized as the expiration-start point $P_e$.

The above-mentioned expiratory period is defined as the period $T_e$ from the expiration-start point $P_{e1}$ to the inspiration-start point $P_i$, and the gradient $\lambda$ is positive during this expiration period $T_e$. The above-mentioned inspiratory period is defined as the period $T_i$ from the ispiration-start point $P_i$ to the inspiration-start point $P_{e2}$, and the gradient $\lambda$ is negative during this inspiratory period $T_i$. The respiration period, which is the sum of the expiratory period $T_e$ and the inspiratory period $T_i$, depends on the individual living body, and it varies in response to actions of the living body such as his physical exercise. In operation, an average expiratory period $T_e$ and an average inspiratory period $T_i$ over several respirations immediately before each controlling time are determined, and such average periods are used as the bases for arithmetic operations for the gas flow control. The reason for using the average expiratory time $T_e$ and the average inspiratory time $T_i$ as the bases is to follow closely to the variation of the respiration periods due to personal difference and due to time elapse in controlling the gas flow in synchronism with the breathing.

In the device and method for gas insufflation according to the present invention, an arbitrary percentage A % (A being less than 100) is set in the memory of the CPU 19 through the input means 23, so that CPU 19 determines the time length equivalent to A % of the average expiratory time $T_e$ at each expiration. Toward the end of the expiratory period, the insufflation of the desired gas (e.g., oxygen gas) is started prior to the inspiration-start point $P_i$ by the above-mentioned time length equivalent to A % of the average expiratory time $T_e$, so that residuals of the expired air in the nasal cavity and the like is replaced by the thus insufflated gas (e.g., oxygen). The time for starting the gas insufflation is determined at the expirationstart point $P_e$, by calculating the time length of $T_e \times (1 - A/100)$, setting this time length on a timer (not shown) of the CPU 19, and starting the count-down of this timer at the expiration-start point $P_e$. When the count of the timer becomes zero, the CPU 19 delivers a control signal on the line 20, so as to actuate the first gas flow controller 3, and the flow of the gas (e.g., oxygen) at a steady flow rate is initiated as shown in FIG. 2D.

Another arbitrary percentage B % (B being less than 100) is set in the memory of the CPU 19 through the input means 23, so that CPU 19 determines the time length equivalent to B % of the average inspiratory time $T_i$ at each inspiration. Toward the end of the inspiratory period, the insufflation of the desired gas (e.g., oxygen gas) is terminated prior to the expiration-start point $P_e$ by the above-mentioned time length equivalent to B % of the average inspiratory time $T_i$. The time for terminating the gas insufflation is determined at the inspiration-start point $P_i$, by calculating the time length of $T_i \times (1 - B/100)$, setting this time length on a timer (not shown) of the CPU 1, and starting the count-down of this timer at the inspiration-start point $P_i$. When the count of the timer becomes zero, the CPU 19 delivers a control signal on the line 20, so as to block the first gas flow controller 3, and the flow of the gas (e.g., oxygen) at a steady flow rate is terminated as shown in FIG. 2D.

If the actual expiratory phase starts before the predetermined gas-insufflation-terminating time as calculated by the program in the operational controller 18, the gas insufflation is terminated at the expiration-start point $P_{e2}$. On the other hand, if the gradient λ of the respiration signal waveform is maintained at the maximum gradient even after the count of the above-mentioned timer of the CPU 19 is counted down to zero, due to deep and slow breathing by the patient 16 or the like, the gas insufflation may be continued even after the pre-estimated expiration-start point $P_e$ and the gas insufflation may be terminated after the maximum gradient condition is over.

Although the gradient change of the respiration signal waveform varies depending on the individual living body, actual measurements indicate that the normal respiration pattern for one living body is substantially constant, and both the expiratory phase and the inspiratory phase of the respiration have substantially identical maximum gradients and the maximum gradient conditions last only for a certain period of time. This certain period of time is the period in which the expired gas and the inspired gas continuously maintain the peak flow rates at the nostril. The maximum gradients are measured for both the expiratory phase and the inspiratory phase, and the average maximum gradients over several respiration cycles immediately prior to the control moment are determined. When the gradient of a measured respiration signal waveform falls in a predetermined allowable error range of the average maximum gradient, it is assumed that the inspiration or expiration "has entered the maximum gradient conditions" or "is maintaining the maximum gradient."

It is noted that the time at which the inspired gas volume curve starts an increase coincides with the time at which the absolute value of the gradient of the respiration signal starts to increase. Accordingly, when the inspiration "has entered the maximum gradient conditions" as described above, the CPU 19 delivers a control signal on the line 21, which control signal actuates the second gas flow controller 4 for a duration P set by the input means 23. Although the period P is comparatively short, the throttle valve 7 of the second gas flow controller 4 is adjusted so as to allow a large flow rate, and the gas is insufflated at a maximum flow rate when the inspiration is maximized, whereby the efficiency of gas inhalation is greatly improved. Since the respiration pattern varies depending on individual living bodies due to differences of breathing capacity, respiration rhythm, the dead space volume, and the like of individual living body, the above-mentioned exhalation gas replacing percentage A, the insufflation reduction percentage B, and the pulse-like insufflation duration P can be set at an arbitrary value, so that the conditions for maximum gas-inhalation efficiency can be easily set while considering the aspiration pattern of individual living body.

As described in detail in the foregoing, a breath-synchronized gas-insufflation device according to the invention divides the gas from a gas source into two passages, one for gas flow control at a steady flow rate and the other one for short pulse-like gas flow control. With the gas flow control at a steady flow rate, the gas insufflation starts before the beginning of the inspiration so as to remove the residuals of the expired air from said spaces, and the concentration of the desired gas in the inspired air reaching the deepest portion of the respiratory organ can be sufficiently raised at the early stage of the inspiration so that the gas-inhalation efficiency can be high, and the gas-inhalation efficiency is greatly improved as compared with that of the prior art.

Besides, the gas flow control at a steady flow rate stops the gas insufflation before the beginning of the expiration, so that the gas to be trapped in the dead space of internal cavity of the living body without being utilized and expelled to the outside in the succeeding exhalation is provided from the atmosphere. whereby the gas consumption is greatly reduced. Further, the pulse-like gas flow control allows superposition of peak gas insufflation on the maximum inhaling period of the inspiratory phase, so that the gas-inhalation efficiency can be further improved.

What is claimed is:

1. A breath-synchronized gas-insufflation device, comprising a gas source, a valve means connected to the gas source so as to regulate flow rate and duration of gas flow from the gas source, an insufflating means connected to the valve means so as to insufflate the gas therefrom toward a respiratory system of a living body, a sensor exposed to respiration of the living body and producing electric signals which distinctively indicate inspiratory phase and expiratory phase of the respiration, and an operational controller receiving the electric signals from the sensor and producing such control signals to the valve means that gas insufflation starts before beginning of the inspiratory phase and ends before termination of the inspiratory phase while providing a short pulse-like peak flow of a large amount of the gas in an early stage of the inspiratory phase.

2. A breath-synchronized gas-insufflation device as set forth in claim 1, wherein said valve means includes a combination of a throttle valve controlling intermittent constant-magnitude flow of the gas and a solenoid valve controlling the short pulse-like peak flow of the gas, which are separately adjustable.

3. A breath-synchronized gas-insufflatin device as set forth in claim 1, wherein said valve means includes two valve lines extending between the gas source and the insufflating means in parallel to each other so as to concurrently apply outputs of the two valve lines to the gas insufflating means, each of the two valve lines having a combination of a throttle valve and a solenoid valve, one of the two valve lines controlling the intermittent constant-magnitude flow of the gas while the other valve line controlling the short pulse-like peak flow of the gas, which are independently controllable.

4. A method for intermittently insufflating a gas from a gas source to respiratory system of living body in synchronism with breathing of the living body, comprising steps of starting the gas insufflation before beginning of inspiratory phase of the breathing of the living body, increasing the flow rate of the gas for a short period substantially simultaneously with the beginning of the inspiratory phase, and ending the gas insufflation before termination of the inspiratory phase of the breathing.

5. A method for intermittently insufflating a gas from a gas source to respiratory system of living body as set forth in claim 4, wherein the gas insufflation is effected substantially at a constant flow rate from said starting to said ending thereof except superposition of a short pulse-like flow of the gas thereto substantially simultaneously with said beginning of the inspiratory phase.

* * * * *